(12) United States Patent
Fabien et al.

(10) Patent No.: US 11,305,062 B2
(45) Date of Patent: Apr. 19, 2022

(54) AUTO-INJECTOR

(71) Applicant: APTAR FRANCE SAS, Le Neubourg (FR)

(72) Inventors: David Fabien, Plouarzel (FR); Olivier His, Saint Etienne du Vauvray (FR); Anthony Saussaye, Louviers (FR)

(73) Assignee: APTAR FRANCE SAS, Le Neubourg (FR)

( * ) Notice: Subject to any disclaimer, the term of this patent is extended or adjusted under 35 U.S.C. 154(b) by 873 days.

(21) Appl. No.: 15/761,471

(22) PCT Filed: Sep. 20, 2016

(86) PCT No.: PCT/FR2016/052384
§ 371 (c)(1),
(2) Date: Mar. 20, 2018

(87) PCT Pub. No.: WO2017/051113
PCT Pub. Date: Mar. 30, 2017

(65) Prior Publication Data
US 2018/0264196 A1  Sep. 20, 2018

(30) Foreign Application Priority Data

Sep. 22, 2015 (FR) ........................... 1558927

(51) Int. Cl.
*A61M 5/20* (2006.01)
*A61M 5/32* (2006.01)

(52) U.S. Cl.
CPC ........ *A61M 5/2033* (2013.01); *A61M 5/3202* (2013.01); *A61M 5/3204* (2013.01);
(Continued)

(58) Field of Classification Search
CPC .............. A61M 5/2033; A61M 5/3202; A61M 5/3204; A61M 5/3213
See application file for complete search history.

(56) References Cited

U.S. PATENT DOCUMENTS

2004/0236284 A1* 11/2004 Hoste ................... A61M 5/326
604/198
2014/0088505 A1* 3/2014 Fabien .............. A61M 39/1055
604/135

FOREIGN PATENT DOCUMENTS

FR    2 884 722 A1    10/2006
GB    2 410 188 A      7/2005
(Continued)

OTHER PUBLICATIONS

International Search Report for PCT/FR2016/052384 dated Dec. 19, 2016 [PCT/ISA/210].
(Continued)

*Primary Examiner* — Scott J Medway
*Assistant Examiner* — John A Doubrava
(74) *Attorney, Agent, or Firm* — Sughrue Mion, PLLC

(57) ABSTRACT

An autoinjector comprising a body (1) that is adapted to receive a reservoir (S), said reservoir (S) containing fluid and including a piston (P) and a needle (A), such as a pre-filled syringe, said autoinjector further comprising an actuator sleeve (10) that is movable relative to said body (1) between projecting positions in which said actuator sleeve (10) projects out from said body (1) at least in part, and an actuated position in which said actuator sleeve (10) is moved axially into said body (1), said actuator sleeve (10) being in a first projecting position before actuation of the autoinjector, and in a second projecting position after actuation of the autoinjector; said actuator sleeve (10) being urged towards said projecting positions by a spring (9), said autoinjector including a removable cap (20) that is fastened to said body (1) before the autoinjector is used, said removable cap (20), when it is fastened to said body (1), moving said actuator sleeve (10) axially relative to said first projecting position through a distance (d) into said body (1), against the force of said spring (9), such that when said removable cap (20) is removed from said body (1), said spring (9) returns said into said first projecting position.

11 Claims, 3 Drawing Sheets

(52) U.S. Cl.
CPC ............... *A61M 2005/206* (2013.01); *A61M 2005/2013* (2013.01); *A61M 2005/2073* (2013.01)

(56) References Cited

FOREIGN PATENT DOCUMENTS

| | | |
|---|---|---|
| WO | 96/32974 A1 | 10/1996 |
| WO | 2009/007229 A1 | 1/2009 |
| WO | 2011/123024 A1 | 10/2011 |
| WO | 2012/000832 A1 | 1/2012 |
| WO | 2012/045833 A1 | 4/2012 |
| WO | 2013/048310 A1 | 4/2013 |
| WO | 2013/175140 A1 | 11/2013 |
| WO | 2013/175142 A1 | 11/2013 |
| WO | 2013/175148 A1 | 11/2013 |
| WO | 2015/075399 A1 | 5/2015 |
| WO | 2015/155484 A1 | 10/2015 |

OTHER PUBLICATIONS

English translation of the International Preliminary Report on Patentability dated Mar. 29, 2018 in counterpart international application No. PCT/FR2016/052384.

* cited by examiner

AUTO-INJECTOR

CROSS REFERENCE TO RELATED APPLICATIONS

This application is a National Stage of International Application No. PCT/FR2016/052384 filed Sep. 20, 2016, claiming priority based on French Patent Application No. 15 58927 filed Sep. 22, 2015.

The present invention relates to an autoinjector.

Autoinjectors are well known in the prior art. The purpose of such devices is mainly to inject the contents of a syringe automatically into a patient's body. Various systems exist for making the penetration of the needle into the body of the patient and the injection of the fluid contained in the syringe automatic. Autoinjectors are relatively complex devices that must satisfy a certain number of constraint requirements in order to be reliable. The robustness of the device, its handling, and its ease of use for the user are also important elements. In addition, since most autoinjectors are for single use, the cost of manufacture and of assembly is also a factor that needs to be taken into account.

Numerous autoinjectors exist on the market, but they all present a certain number of drawbacks.

Thus, in order to avoid the autoinjector being triggered accidentally, e.g. during transport or during storage, the devices should include reliable locking means. In addition, when a user wishes to use the autoinjector, the device should not be triggered accidentally, but only when the user actually wishes it, i.e. when the user applies it against the part of the body where injection is to be performed. Unfortunately, in particular when the people using an autoinjector are elderly or handicapped people, the user may drop the device when it is to be used. In such circumstances, it is desirable that the autoinjector does not trigger itself. It is thus important to provide a reliable trigger lock. Equally, use of the autoinjector must not become too difficult, as this would prevent weak people from using it. Furthermore, in order to avoid any risk of injury after using the device, the autoinjector should include a needle safety device that avoids the needle remaining visible after the device has been used. Obviously, the safety device should also be reliable and not be released too easily. It should also be functional even when the user actuates the autoinjector poorly, e.g. when the user removes it too soon from the body, before the end of injection.

Unfortunately, autoinjectors are sometimes used rather a long time after being assembled, and it is thus important for the various component parts, and in particular the trigger lock and the needle safety device, to remain functional in reliable manner even after a long period of storage. An object of the present invention is to satisfy this problem.

Documents WO 2013/175140, WO 2013/175142, WO 2015/075399, WO 2012/045833, FR 2 884 722, WO 96/32974, and WO 2012/000832 describe prior-art devices.

An object of the present invention is to provide an autoinjector that does not have the above-mentioned drawbacks, and that makes it possible to satisfy the various major requirements and constraints for safe and reliable use of the autoinjector.

Another object of the present invention is to provide an autoinjector that is reliable in use, that is safe and that prevents any risk of injury, even after a long period of storage, and that is simple and inexpensive to manufacture and to assemble.

The present invention thus provides an autoinjector comprising a body that is adapted to receive a reservoir, said reservoir containing fluid and including a piston and a needle, such as a pre-filled syringe, said autoinjector further comprising an actuator sleeve that is movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the auto-injector; said actuator sleeve being urged towards said projecting positions by a spring, said autoinjector including a removable cap that is fastened to said body before the autoinjector is used, said removable cap, when it is fastened to said body, moving said actuator sleeve axially relative to said first projecting position through a distance d into said body, against the force of said spring, such that when said removable cap is removed from said body, said spring returns said into said first projecting position.

Advantageously, one of said actuator sleeve and said body includes a flexible tab that is adapted to deform sideways and/or radially relative to said actuator sleeve and/or relative to said body when said actuator sleeve is moved, the other one of said actuator sleeve and said body including a guide profile that co-operates with said flexible tab while said actuator sleeve is moving.

Advantageously, said flexible tab is deformed sideways and/or radially relative to said actuator sleeve and/or relative to said body when said actuator sleeve is moved from its first projecting position to its actuated position, and then from its actuated position while returning to its second projecting position.

Advantageously, said guide profile includes an initial groove that is defined at least in part by a shoulder that co-operates with said flexible tab when said actuator sleeve is in said first projecting position.

Advantageously, in said first projecting position, the force of said spring is exerted on the contact point between said flexible tab and said shoulder.

Advantageously, said removable cap includes fastener means for fastening on said body.

Advantageously, said fastener means comprise a fastener profile, such as an inwardly-projecting radial bead, that co-operates with a complementary outer portion of said body, typically an outwardly-projecting radial bead.

Advantageously, said fastener means comprise two axial tabs that are diametrically-opposite and that extend around said body, each axial tab including a fastener profile.

Advantageously, said actuator sleeve includes a contact end for coming into contact with the user's body.

Advantageously, said body includes said flexible tab, and said actuator sleeve includes said guide profile.

In a variant, said body includes said guide profile, and said actuator sleeve includes said flexible tab.

These characteristics and advantages and others of the present invention appear more clearly from the following detailed description, given by way of non-limiting examples, and with reference to the accompanying drawings, and in which:

FIG. 1*a* is a diagrammatic side view of an autoinjector constituting an advantageous embodiment of the present invention, before removal of the protective cap;

FIG. 1*b* is a partially cut-away diagrammatic side view of the FIG. 1*a* autoinjector, seen from another direction;

FIG. 1*c* is a fragmentary and diagrammatic section view of the autoinjector in FIGS. 1*a* and 1*b*;

FIG. 1*d* is a fragmentary and diagrammatic view of a detail of the cut-away portion in FIG. 1*b*;

Figure 1A:
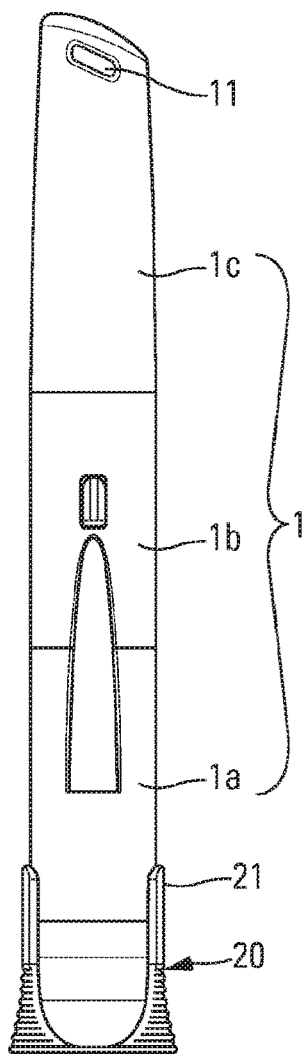
Figure 1B:
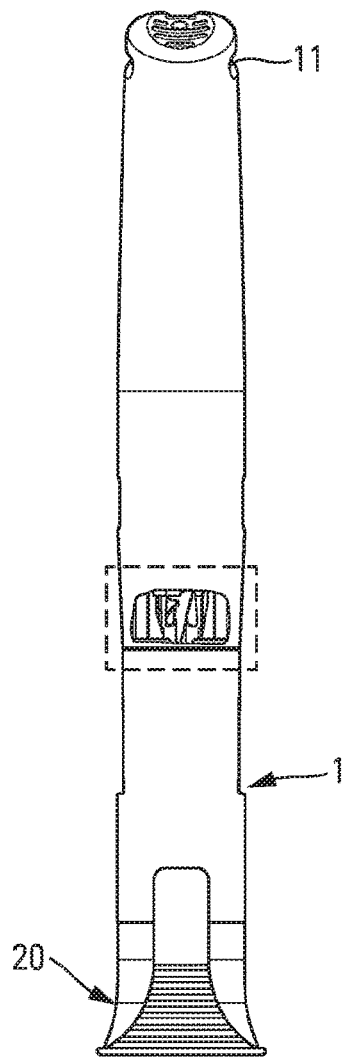

In the following description, the terms "top", "bottom", "high", and "low" refer to the positions shown in the figures. The terms "proximal" and "distal" are relative to the needle of the autoinjector. The terms "axial" and "radial" refer to the longitudinal central axis X shown in FIG. 1c.

The autoinjector is described below with reference to an advantageous embodiment. It should nevertheless be observed that autoinjectors, which are complex appliances, comprise a plurality of modules for performing a plurality of functions. The various modules may be used separately and independently of one another, without necessarily being combined with the other modules, and in particular they could be used in autoinjectors of shape that is different from the shape shown in the drawings. Furthermore, it should be observed that the drawings are diagrammatic views, which do not necessarily represent the exact shape of the components of an autoinjector, and they are not necessarily to scale, in particular for purposes of clarity. In addition, the drawings do not necessarily represent all of the component elements of an autoinjector, but only the elements necessary for operation of the present invention. Thus, various additional and/or complementary elements and modules could be associated with the autoinjector shown in the figures.

Figure 1C:
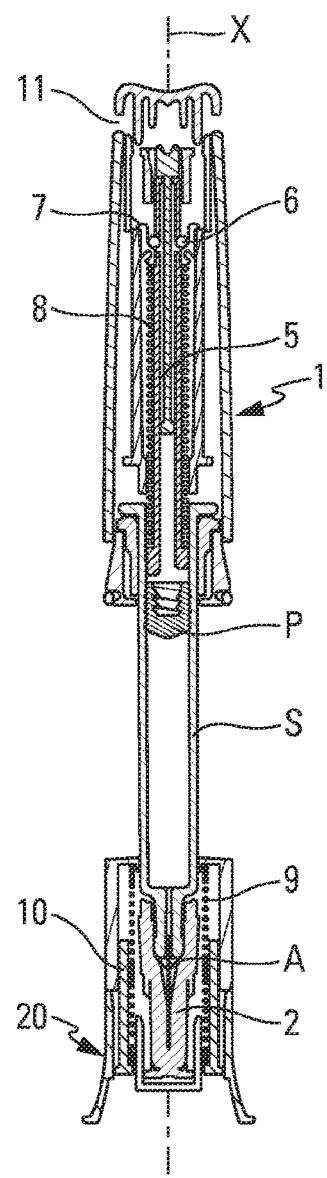
Figure 2A:
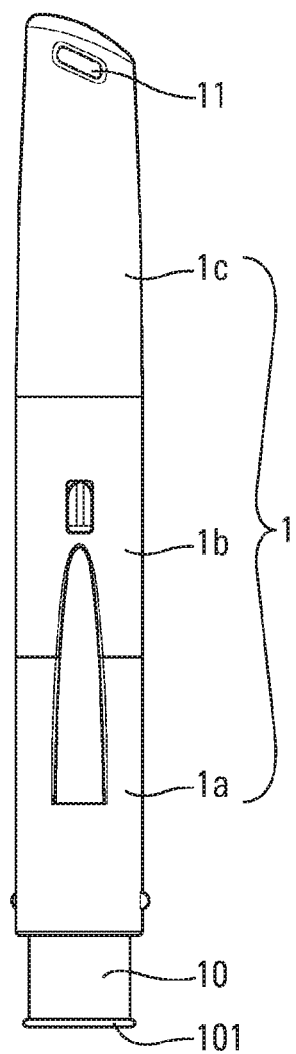
FIGS. 2a to 2d are views similar to the views in FIGS. 1a to 1d respectively, after removal of the protective cap and before actuation of the autoinjector.

The autoinjector shown in the figures comprises a body 1 in which an actuator sleeve 10 slides axially, the actuator sleeve 10 having a bottom end 101 that is for coming into contact with the body of the patient around the injection zone. In the embodiment shown in the figures, the autoinjector includes a lower body 1a, an intermediate body 1b, and an upper body 1c that are assembled together so as to form the body 1 of the autoinjector, as indicated in FIGS. 1a and 2a. Below, the term "body" and the numerical reference "1" are used to designate said unitary body formed by assembling said lower body 1a with said intermediate body 1b and said upper body 1c. It should be observed that the body 1 could be formed of any number of body portions, e.g. two, and that the embodiment in the figures, with three body portions, is not limiting.

A reservoir S is inserted into said autoinjector. The reservoir S contains fluid and includes a piston P and a needle A. The piston P is adapted to move in said reservoir S so as to inject the fluid through said needle A. The present description is made with reference to a syringe S that may be of any type. More generally, it is understood that the term "syringe" in the present description encompasses any type of reservoir associated with a needle. Preferably, the reservoir S is a pre-filled syringe.

The autoinjector also includes an automatic injection system, in particular comprising a piston rod 5 that is adapted to co-operate with the piston P so as to move it in the reservoir S so as to dispense the fluid through the needle A. Conventionally, the piston rod 5 is urged by an injection spring 8 towards its dispensing position and, before actuation, it is held in its rest position by an appropriate injection lock. Examples of advantageous injection locks are described in particular in documents WO 2013/175148 and PCT/FR2015/050940 which is a co-pending application. As can be seen in very diagrammatic manner in FIGS. 1c and 2c, the injection lock may comprise at least one (and preferably three) blocking element 6 held in the blocking position by a blocking ring 7. Said piston rod 5 may include a radial recess that receives said blocking elements that are movable between a blocking position and an unblocking position. Said blocking elements are preferably substantially spherical in shape, such as balls. Advantageously, said balls are urged radially outwards by said piston rod 5 and they are held in their blocking position by said blocking ring 7. The blocking ring 7 is movable axially upwards relative to said piston rod 5 between a locking position in which it holds said balls in their blocking position, and an unlocking position in which said balls are released, thus unblocking said injection lock and enabling said injection spring 8 to move said piston rod 5 towards its injection position. Advantageously, when the needle A of the syringe S has penetrated the user's body, the blocking ring 7 is moved axially upwards, thereby causing the balls to be released from their blocking position, said balls then moving radially outwards. The piston rod 5 is then no longer held by the balls, and it is thus moved axially downwards so as to inject the fluid.

The autoinjector may also include a visual, audible, and/or tactile indicator device for indicating to the user, in particular by an audible sound, by vibration, and/or by visual and/or tactile indication, that the autoinjector may be removed from the injection site. In particular, the indicator device may include one or more indicator elements that give both a visual indication, by a suitable display in one or more windows 11 of the body 1, and also an audible and/or tactile indication.

Figure 2B:
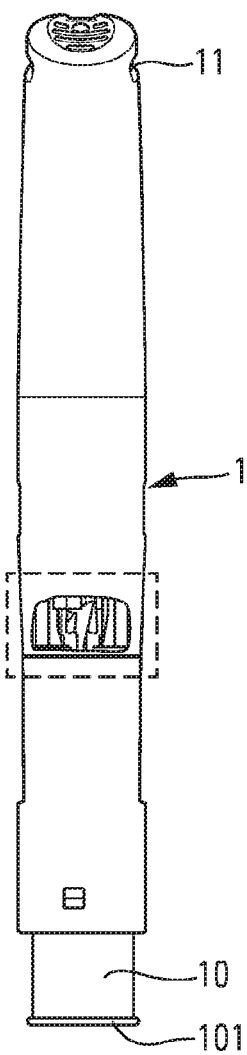
Figure 2C:
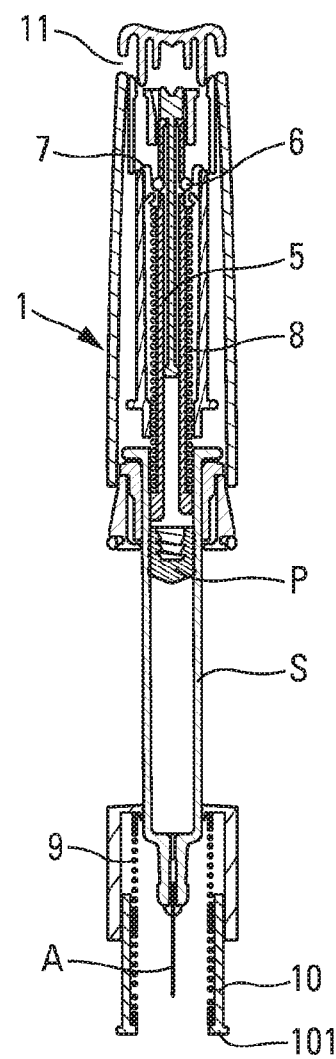

The actuator sleeve 10 is urged towards its projecting positions by a spring 9 that may be of any type. The spring 9 co-operates both with said actuator sleeve 10 and also with a portion 12 that is secured to the body 1. Before actuation, the actuator sleeve 10 is in a first projecting position in which it surrounds the needle A, as shown in FIGS. 2a to 2c. During actuation, the actuator sleeve 10 slides inside the body 1 towards an actuated position, so as to expose the needle A and enable pricking, and then injection of the fluid. After injection, when the user removes the autoinjector from the injection site, the actuator sleeve 10 returns into an end-of-use second projecting position in which it is once again arranged around the needle A, so as to avoid any risk of injury with said needle. It should be observed that the first and second projecting positions of the actuator sleeve 10 may be positions that are different or that are identical.

In the invention, the autoinjector includes a removable cap 20 that the user must remove before actuation.

Before the autoinjector is used, the needle A of the syringe S is advantageously protected by a guard 2, typically made out of elastomer, into which the end of the needle is poked. In this configuration, removing said removable cap 20 advantageously causes said guard 2 to be removed from the needle A.

Said cap 20 includes fastener means 21 that fasten on the proximal portion of said body 1. Advantageously, said fastener means 21 comprise a fastener profile 25, such as an inwardly-projecting radial bead, that co-operates with a complementary outer portion 15 of said body 1, typically an outwardly-projecting radial bead. Thus, co-operation between said beads 15 and 25 holds said removable cap 20 on said body 1, and the user must exert an axial force (that can be predetermined), so as to be able to disengage said cap 20 from said body 1.

Figure 3A:
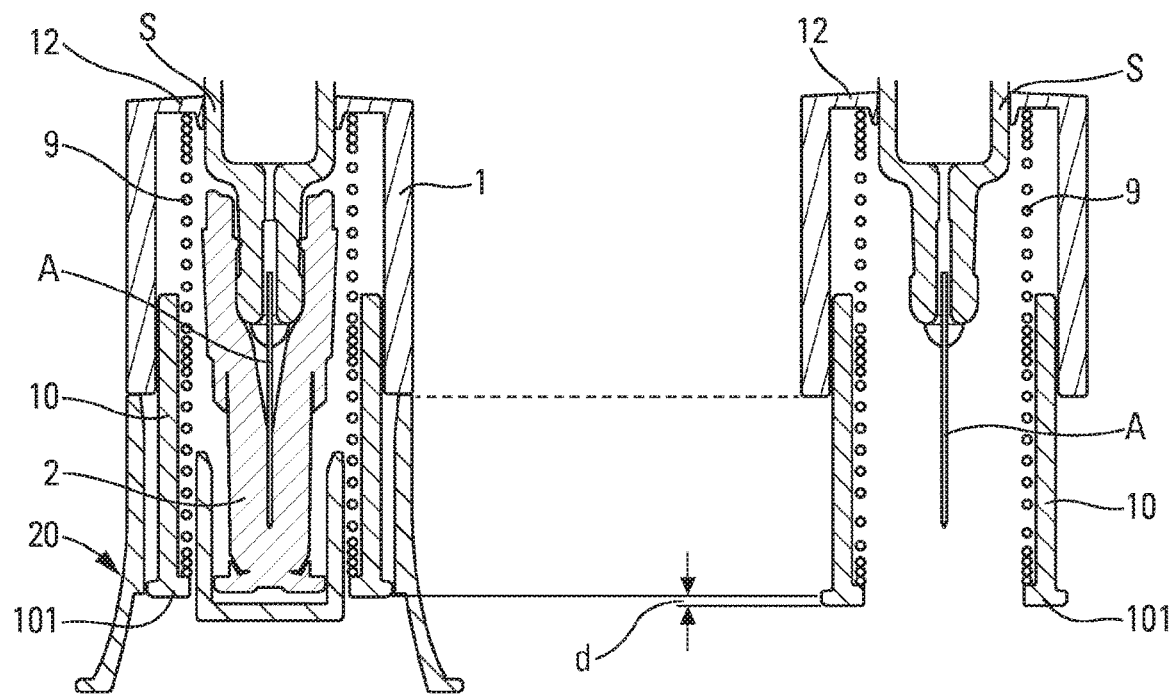
FIG. 3a is a diagrammatic view of a detail of the proximal portion of the autoinjector, comparing the positions before and after removal of the protective cap.
Figure 3B:
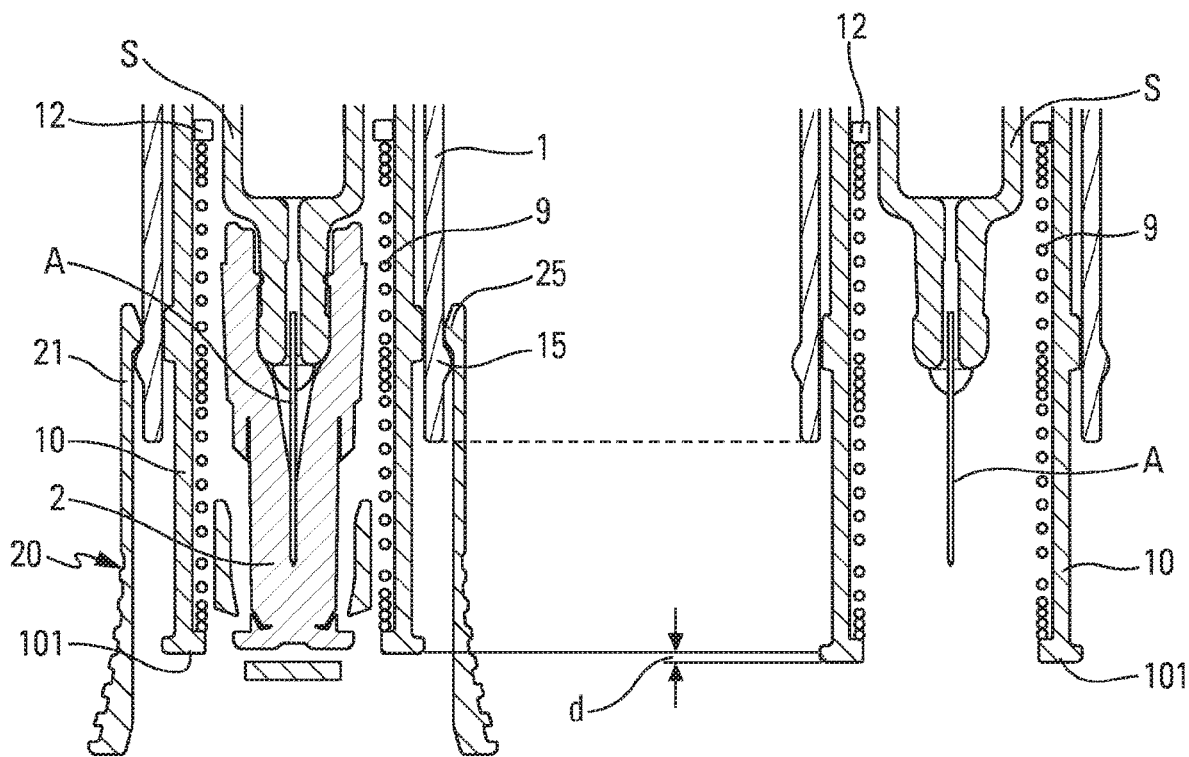
FIG. 3b is a view similar to the view in FIG. 3a, seen from another direction.

Advantageously, said fastener means 21 comprise two axial tabs that are diametrically-opposite and that extend around said body 1, each axial tab including a fastener profile 25, as can be seen in FIGS. 1a and 3b.

The actuator sleeve 10 includes a guide profile comprising grooves, in particular an initial groove 100, and the body 1 includes a flexible tab 110 that co-operates with the grooves of the actuator sleeve 10 when said actuator sleeve moves relative to the body 1 while the autoinjector is being actuated. This co-operation between the flexible tab 110 of the body 1 and the guide profile of the actuator sleeve 10 makes it possible to provide both the trigger lock for use at the start of actuation, and the lock for securing the safety position, corresponding to the second projecting position of said actuator sleeve.

As described in particular in documents WO 2013/175140, WO 2013/175142, and WO 2015/075399, the flexible tab 110 moves sideways and/or radially in said guide profile so as to ensure that the autoinjector is triggered and then locked, and it is thus important that the flexible tab functions in reliable manner. Unfortunately, before actuation, and without a removable cap 20, the spring 9 urges the actuator sleeve towards its first projecting position, and the head of the flexible tab 110 is thus under stress from said spring at the contact point C between said head of the flexible tab 110 and the shoulder 13 of the body 1 that defines an end wall of said guide profile, and in particular of the initial groove 100. The contact point C can be seen clearly in FIG. 2d.

Unfortunately, the forces exerted by the spring 9 at the contact point C, tend to lengthen the flexible tab 110 by deforming it axially. This tension may spoil the strength properties of the flexible tab 110, and thus degrade its performance, in particular concerning its strength while in the needle safety position at the end of actuation. The longer this tension is maintained over time, the greater the risk of degradation. Storing the autoinjector for a long period before use thus increases this risk.

In the invention, fastening the removable cap 20 on the body 1 causes the actuator sleeve 10 to move axially upwards, thereby relieving said flexible tab from being subjected to stress by the spring 9.

Figure 1D:
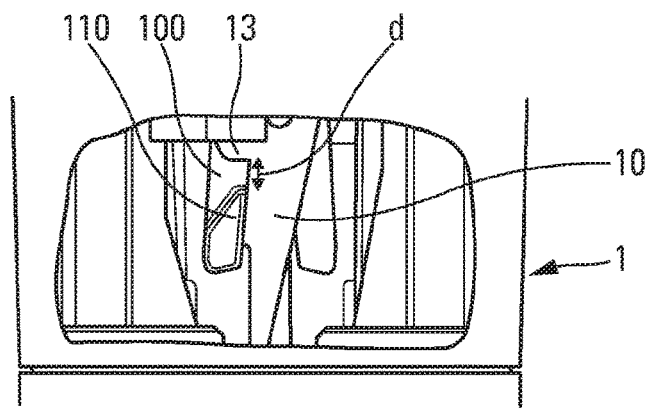

More precisely, when the removable cap 20 is fastened to the body 1, the actuator sleeve 10 is moved axially upwards (i.e. towards the distal portion of the body 1), through a distance d, thereby compressing the spring 9 a little. As can be seen in FIG. 1d, there is thus no contact between the shoulder 13 of the body 1 and the head of the flexible tab 110, and this relieves said flexible tab from being subjected to the axial stresses exerted by the spring 9. The fastening of the removable cap 20 on the body 1 must thus be stronger than the force exerted on the actuator sleeve 10 by the spring 9. Specifically, in the absence of a contact point between the flexible tab 110 and the shoulder 13 of the body 1, the force of the spring 9 is exerted on the removable cap 20 that holds the actuator sleeve in the position that is offset upwards by the distance d. More precisely, the force is thus applied on the fastener means for fastening the removable cap 20 on the body 1, i.e. in the embodiment shown, on the beads 15 and 25 as can be seen in FIG. 3b. The user must thus pull axially downwards on said removable cap 20 with an axial force that is greater than the force exerted by the spring 9, so as to be able to remove said cap from the body 1.

Figure 2D:
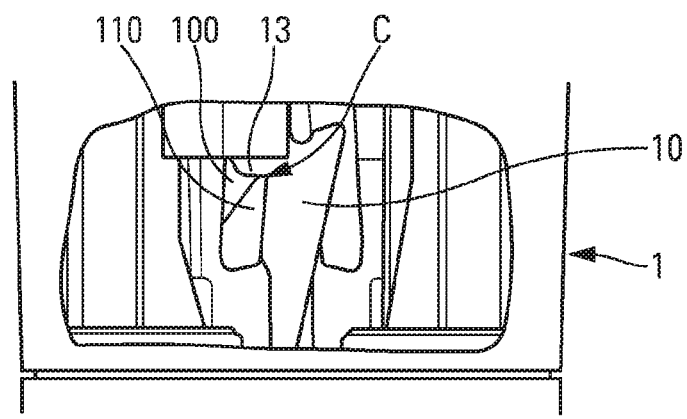

When the user removes said removable cap 20, the spring 9 moves said actuator sleeve axially downwards through said distance d, and brings it into said first projecting position in which the head of the flexible tab 110 comes into contact with said shoulder 13 of the body 1, as can be seen in FIG. 2d.

From two different directions, FIGS. 3a and 3b show said upward movement, through a distance d, of the actuator sleeve 10 when the removable cap 20 is fastened to the body 1, by comparing the position with the cap on the lefthand sides and the position without the cap on the righthand sides of the figures.

Both of the locks of the actuator sleeve, namely the trigger lock for locking the trigger before actuation and the lock for securing the injector after actuation are thus particularly effective and reliable, while being robust and easy, and thus inexpensive, to mold and to assemble. In particular, they comprise only two parts, the actuator sleeve 10 and the body 1.

Naturally, the shapes of the guide profile and of the flexible tab may be modified as a function of the needs and the characteristics that are desired.

It should be observed that the above-described means could be achieved in inverted manner, i.e. the body 1 could include the guide profile, and in particular the initial groove 100, and the actuator sleeve 10 could include the flexible tab 110.

The present invention applies to devices used in particular for treatment of auto-immune diseases, e.g. of the rheumatoid arthritis, multiple scleroses, Crohn's disease type, for treatment of cancer, for antiviral treatments, e.g. of the hepatitis type, for treatment of diabetes, for treatment of anemia, or for treatment of allergy attacks, e.g. in the event of anaphylactic shock.

Although the present invention is described above with reference to an advantageous embodiment, naturally various modifications can be applied thereto by the person skilled in the art, without going beyond the ambit of the present invention, as defined by the accompanying claims.

The invention claimed is:

1. An autoinjector comprising a body that is adapted to receive a reservoir (S), said reservoir (S) containing fluid and including a piston (P) and a needle (A), said autoinjector further comprising an actuator sleeve that is movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector; said actuator sleeve being urged towards said projecting positions by a spring, said autoinjector including a removable cap that is fastened to said body before the autoinjector is used, wherein said removable cap, when fastened to said body, co-operates with said actuator sleeve so that said actuator sleeve is moved axially relative to said first projecting position through a distance (d) into said body, against a force of said spring, such that when said removable cap is removed from said body, said spring urges said actuator sleeve into said first projecting position, wherein one of said actuator sleeve and said body includes a flexible tab that is adapted to deform sideways and/or radially relative to said actuator sleeve and/or relative to said body when said actuator sleeve is moved, the other one of said actuator sleeve and said body including a guide profile that co-operates with said flexible tab while said actuator sleeve is moving, said guide profile including an initial groove that is defined at least in part by a shoulder that co-operates with said flexible tab when said actuator sleeve is in said first projecting position, and wherein, in said first projecting position, said flexible tab contacts said shoulder at a contact point (C), such that said spring urges said flexible tab axially into contact with said contact point.

2. The autoinjector according to claim 1, wherein said flexible tab is deformed sideways and/or radially relative to said actuator sleeve and/or relative to said body when said actuator sleeve is moved from its first projecting position to its actuated position, and then from its actuated position while returning to its second projecting position.

3. The autoinjector according to claim 1, wherein said removable cap includes fastener means for fastening on said body.

4. The autoinjector according to claim 1, wherein said actuator sleeve includes a contact end for coming into contact with the user's body.

5. The autoinjector according to claim 1, wherein said body includes said flexible tab, and said actuator sleeve includes said guide profile.

6. The autoinjector according to claim 1, wherein said body includes said guide profile, and said actuator sleeve includes said flexible tab.

7. The autoinjector according to claim 1, wherein the reservoir containing fluid, the piston and the needle form a pre-filled syringe.

8. The autoinjector according to claim 3, wherein said fastener means comprise a fastener profile, that co-operates with a complementary outer portion of said body.

9. The autoinjector according to claim 3, wherein the fastener profile is an inwardly-projecting radial bead.

10. The autoinjector according to claim 8, wherein said fastener means comprise two axial tabs that are diametrically-opposite and that extend around said body, each axial tab including a fastener profile.

11. The autoinjector according to claim 8, wherein the complementary outer portion of said body is an outwardly-projecting radial bead.

* * * * *